(12) United States Patent
Rice et al.

(10) Patent No.: US 8,594,764 B2
(45) Date of Patent: Nov. 26, 2013

(54) DEVICE AND METHOD FOR ASSESSING THE ELECTRICAL POTENTIAL OF CELLS AND METHOD FOR MANUFACTURE OF SAME

(76) Inventors: Jon Rice, Rancho Murieta, CA (US); Barry H. Hirschowitz, Sacramento, CA (US)

( * ) Notice: Subject to any disclaimer, the term of this patent is extended or adjusted under 35 U.S.C. 154(b) by 1951 days.

(21) Appl. No.: 10/794,854

(22) Filed: Mar. 5, 2004

(65) Prior Publication Data
US 2004/0176675 A1 Sep. 9, 2004

Related U.S. Application Data

(60) Provisional application No. 60/542,777, filed on Mar. 7, 2003.

(51) Int. Cl.
*A61B 5/05* (2006.01)
*A61B 5/04* (2006.01)
*H04R 29/00* (2006.01)

(52) U.S. Cl.
USPC .............. 600/407; 600/547; 600/372; 381/56

(58) Field of Classification Search
USPC .......... 600/407, 547, 372, 386; 324/144, 459, 324/463
See application file for complete search history.

(56) References Cited

U.S. PATENT DOCUMENTS

| | | | |
|---|---|---|---|
| 4,291,708 A | 9/1981 | Frei et al. | |
| 4,328,809 A | 5/1982 | Hirschowitz et al. | |
| 4,407,300 A | 10/1983 | Davis | |
| 4,416,288 A | 11/1983 | Freeman | |
| 4,444,199 A | 4/1984 | Shafer | |
| 4,486,835 A | 12/1984 | Bai et al. | |
| 4,557,271 A | 12/1985 | Stoller et al. | |
| 4,578,635 A | 3/1986 | Mee et al. | |
| 4,641,649 A | 2/1987 | Walinsky et al. | |
| 4,695,362 A * | 9/1987 | Kissel | 204/419 |
| 4,793,355 A | 12/1988 | Crum et al. | |

(Continued)

FOREIGN PATENT DOCUMENTS

| WO | WO2005/086724 A2 | 9/2005 |
|---|---|---|
| WO | WO2005/086724 A3 | 3/2006 |

OTHER PUBLICATIONS

Cuzick, J., Holland, R., Barth, V., Davis, R., Faupel, M., Fentiman., Frischbier, H.J., MaMarque, J.L., Merson, M., Sacchini, V., Vanel, D., Veronesi, U., (1998) Electropotential Measurements as a New Diagnostic Modality For Breast Cancer; The Lancet, vol. 352:359.

(Continued)

*Primary Examiner* — Long V. Le
*Assistant Examiner* — Helene Bor
(74) *Attorney, Agent, or Firm* — Greenberg Traurig LLP; Cecily Anne O'Regan

(57) ABSTRACT

An apparatus and processing method for assessing the electrical potential of cells in a living organism using a high-density sensor array having a density of at least about 9 electrodes per square inch for measuring the potential of the static and quasi-static electromagnetic fields of the group of cells proximal to each electrode, where the array can be placed overlying at least a portion of a surface of a living organism with substantially all of the electrodes electrically contactable with such surface, and the surface overlying a site containing cells of clinical interest.

46 Claims, 9 Drawing Sheets

(56) References Cited

U.S. PATENT DOCUMENTS

| | | | |
|---|---|---|---|
| 4,955,383 | A | 9/1990 | Faupel |
| 5,099,844 | A | 3/1992 | Faupel |
| 5,217,014 | A | 6/1993 | Hahn et al. |
| 5,240,010 | A | 8/1993 | Weinmann |
| 5,269,325 | A | 12/1993 | Robinson et al. |
| 5,272,624 | A | 12/1993 | Gisser et al. |
| 5,311,878 | A | 5/1994 | Brown et al. |
| 5,320,101 | A | 6/1994 | Faupel et al. |
| 5,381,333 | A | 1/1995 | Isaacson et al. |
| 5,409,011 | A | 4/1995 | Alexeev |
| 5,415,164 | A * | 5/1995 | Faupel et al. ............ 600/372 |
| 5,415,629 | A * | 5/1995 | Henley .................. 604/20 |
| 5,427,098 | A | 6/1995 | Faupel |
| 5,465,730 | A | 11/1995 | Zadehkoochak et al. |
| 5,560,357 | A | 10/1996 | Faupel |
| 5,564,429 | A * | 10/1996 | Bornn et al. ............ 600/508 |
| 5,660,177 | A | 8/1997 | Faupel et al. |
| 5,678,547 | A | 10/1997 | Faupel et al. |
| 5,687,724 | A | 11/1997 | Jewett |
| 5,697,369 | A | 12/1997 | Long, Jr. et al. |
| 5,706,823 | A | 1/1998 | Wodlinger |
| 5,715,821 | A | 2/1998 | Faupel |
| 5,732,710 | A | 3/1998 | Rabinovich et al. |
| 5,823,957 | A | 10/1998 | Faupel et al. |
| 5,865,743 | A | 2/1999 | Godik |
| 6,011,992 | A | 1/2000 | Hubbard et al. |
| 6,165,721 | A * | 12/2000 | Rostkowski et al. ........ 435/6 |
| 6,179,786 | B1 | 1/2001 | Young |
| 6,192,262 | B1 | 2/2001 | Godik |
| 6,256,535 | B1 | 7/2001 | Province et al. |
| 6,292,690 | B1 | 9/2001 | Petrucelli et al. |
| 6,295,468 | B1 | 9/2001 | Hess |
| 6,351,666 | B1 | 2/2002 | Cuzick et al. |
| 6,429,431 | B1 * | 8/2002 | Wilk .................. 250/363.02 |
| 6,438,413 | B1 | 8/2002 | Taheri |
| 6,532,384 | B1 | 3/2003 | Fukuda |
| 6,624,510 | B1 * | 9/2003 | Chan et al. ............ 257/734 |
| 6,633,777 | B2 | 10/2003 | Szopinski et al. |
| 6,666,821 | B2 | 12/2003 | Keimel |
| 6,751,499 | B2 | 6/2004 | Lange et al. |
| 6,829,499 | B1 | 12/2004 | Shahinpoor et al. |
| 2002/0115198 | A1 | 8/2002 | Nerenberg et al. |
| 2002/0128700 | A1 * | 9/2002 | Cross, Jr. ............ 607/117 |
| 2004/0176675 | A1 | 9/2004 | Rice et al. |

OTHER PUBLICATIONS

Weiss BA, Ganepola AP, Freeman HP, Hsu YS, Faupel ML: Surface electrical potentials as a new modality in the diagnosis of breast lesions—a preliminary report. Breast. Dis 1994;7:91-98.

* cited by examiner

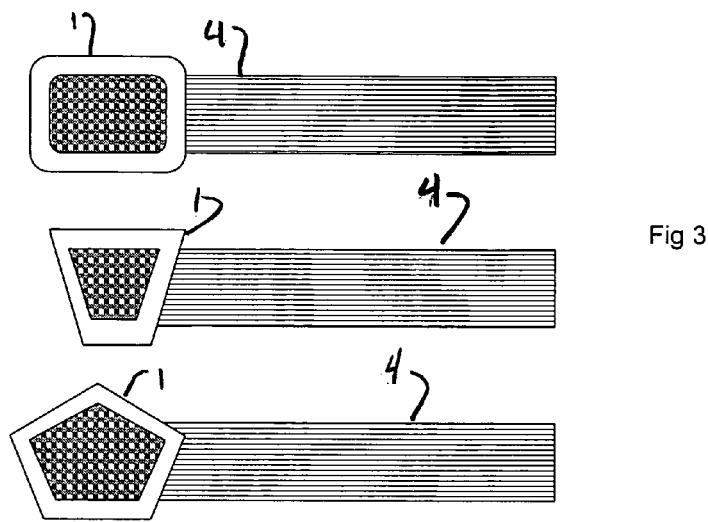
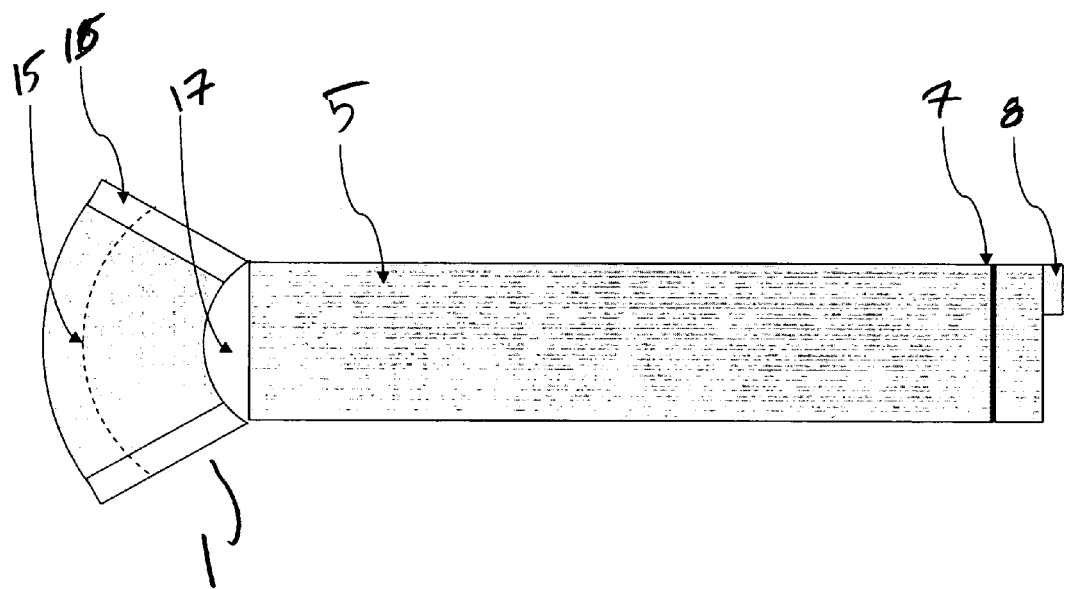
Fig 3
Fig 4

| | |
|---|---|
| Perforate substrate at feed through locations | Step 1 |
| Apply conductive material at feed through locations | Step 2 |
| Apply upper surface with silver-silver chloride conductive material forming electrode lands and conductive traces to the connector end of the tail | Step 3 |
| Apply back side with conductive materials forming conductive traces from the electrode feed through to the connector end of the tail | Step 4 |
| Apply die cut adhesive film to top surface outlining the electrode lands and forming the adhesive edge and strain relief noted in Figure 1 | Step 5 |
| Place disks of hydrogel on top of each electrode land | Step 6 |
| Apply die cut release paper to top surface over the adhesive area and seal in an air tight package | Step 7 |

Fig 7

DEVICE AND METHOD FOR ASSESSING THE ELECTRICAL POTENTIAL OF CELLS AND METHOD FOR MANUFACTURE OF SAME

CROSS-REFERENCE

This application claims the benefit of U.S. Provisional Application No. 60/452,777, filed Mar. 7, 2003.

BACKGROUND OF THE INVENTION

1. Field of the Invention

The present invention relates to an apparatus and method for assessing the electrical potential of cells of clinical interest in a living organism using a high-density sensor array system.

2. Background Art

It is well established that transmembrane electrical potentials (sometimes known as electropotentials or biopotentials) in cellular division and in many types of abnormal or cancer cells are markedly different from cells in their normal state. Structural changes in tissue, such as occurs in malignancy, result in changes in electrolyte distribution that can give rise to an abnormal surface charge distribution. Animal and plant cells also have a characteristic profile of ion gradients across the plasma membrane under steady-state conditions.

Malignant cells and normal cells also have different membrane permeabilities which in turn affects the electric potential across the membrane. In 1981, Morris and Hirschowitz published the first clinical study using surface electrical potential measurement to detect human breast cancer. *J Bioelectricity*, 1982, 1:155-159.

Given the types of ionic species in the extracellular and intracellular fluids, the cell cannot be more negative than −92 mV or more positive that +64 mV. In reality, because the cell membrane has a finite permeability to most ionic species, the actual electrical potential difference at any point in time will lay somewhere within these two figures.

While these static and quasi-static potentials are relatively small and often difficult to measure, physiological processes that give rise to rapidly changing potentials are routinely used. Common examples are changes in nerve cell membrane potentials in the brain measured by electro-encephalogram (EEG) arrays, as well as heart functions measured by electro-cardiogram (ECG) devices.

Hirschowitz et al., U.S. Pat. No. 4,328,809, disclosed devices and methods to measure cellular status via analysis of direct current potentials from the surface of the skin. These methods involved the use of individually applied sets, or several sets, of high quality bioelectric sensors. For breast cancer detection, Hirschowitz et al. shows that a test electrode can be placed in each quadrant of a human female breast and that multiple measurements can be taken during a test period with each test electrode and a reference electrode. These multiple measurements are digitized, normalized, and summed to provide an average or mean output signal indicative of a parameter of the living organism under test.

Other electrical potential measuring devices, all utilizing individual electrodes, are shown by U.S. Pat. No. 4,407,300 to Davis, and U.S. Pat. Nos. 4,557,271 and 4,557,273 to Stoller et al. Davis in particular discloses the diagnosis of cancer by measuring the electromotive forces generated between two electrodes applied to a subject.

Measurements of electrical potentials have also been accomplished using geometric arrangements of independent electrodes, with a multiplexing system to switch between electrodes in the arrangement. The aforementioned Hirschowitz et al. patent contemplates the use of a plurality of test electrodes, while U.S. Pat. No. 4,416,288 to Freeman and U.S. Pat. No. 4,486,835, to Bai, disclose other arrangements of measuring electrodes. Using these measurement techniques, U.S. Pat. Nos. 4,955,383 and 5,099,844, Faupel et. al., discloses a method and apparatus using electrical potential differentials between averaged values provided by a plurality of different sensors. This method operates on the basis of maximum differentials between areas of diseased tissue and apparently normal tissue.

However, while clinical results from the continuing human trials for independent sensor set technology demonstrated there were, in fact, bioelectrical changes in the breast indicative of change and cancer, the diagnostic false negative ratios were too high for the technology to be utilized by medical practitioners, independent of how signal analysis was performed.

Efforts have continued to identify a practical alternative diagnostic technology to assess breast lesions, and that could also be applied in the diagnosis of certain other cancers, as well as cellular processes or states, such as inflammation or wound healing.

With regard to breast health, there are only two major methods of detecting suspicious breast tissue. One is a simple physical examination of the breast performed by a woman herself, or by a physician. This type of detection is only relevant for palpable structures. If a suspicious lump is identified, the patient proceeds to biopsy.

The other method is imaging studies, known as mammography. If a mammogram detects a suspicious area, the patient is then sent for follow-up procedures, such as biopsy. However, mammograms are unable to detect rapidly dividing cancer cells prior to their formation into a tumor of a certain density. Additionally, they are painful to women and fail to adequately include portions of the breast because of the compression technique applied.

The American College of Radiology (ACR) employs the standardized Breast Imaging Reporting and Data System (BI-RADS) for reporting mammography results. This diagnostic system remains very subjective, however, with definitions such as "probably benign" and "suspicious abnormality", leaving a lot of room for interpretation and often requiring additional tests. In 90% of suspicious cases, even after diagnostic mammography, a patient will still have to undergo breast biopsy to obtain a specimen for histological diagnosis.

Although surgical biopsy has historically been accepted as the gold standard for histological diagnosis, biopsies have an error rates from 0.2% to as high as 20% [Medicare/Medicaid SCHIP, Medicare Coverage Policy; Breast Biopsy (#CAG-00040) Decision Memorandum, Dec. 7, 1999]. This means that even after a biopsy, a woman may not have a definitive analysis of her condition, leading to either unnecessary mastectomy or misdiagnosed cancer. Other serious drawbacks include the facts that the technique can be disfiguring, time consuming, and expensive.

There are over one million breast biopsies performed in the United States each year. According to multiple clinical studies, American Cancer Society and Medicare Statistics, the biopsy report proves to be benign for 70-80% of all breast biopsies. Therefore, approximately 750 out 1000 women undergo breast biopsies unnecessarily. Exclusion of even 50% of patients from biopsy processes would translate into significant savings, with funds otherwise tied up in biopsy costs used for additional screening of the population and ultimately in the saving of lives.

SUMMARY OF THE INVENTION

By the present invention is provided an apparatus for assessing the electrical potential of cells in a living organism using a high-density sensor array having a density of at least about 9 electrodes per square inch for measuring the potential of the static and quasi-static electromagnetic fields of the group of cells proximal to each electrode, where the array can be placed overlying at least a portion of a surface of a living organism with substantially all of the electrodes electrically contactable with such surface, and the surface overlying a site containing cells of clinical interest.

Array electrodes are referenced to one or more electrodes placed on a part of the organism remote from the array site, such as a limb.

Each of the electrodes of the array comprises a passive electrode capable of detecting static and quasi-static electromagnetic fields of the cells, which are more preferably connected to a source capable of monitoring the electrode integrity.

In a preferred such embodiment, the density of the array is at least about nine electrodes per square inch, reflecting a three square arrangement in the area contactable with the surface. Higher densities of twenty-five electrodes per square inch or even higher densities are also contemplated by the invention.

The total, or overall, density, may be at least about thirty-six electrodes, and more preferably at least about 100 electrodes. In another preferred apparatus of the invention, the high-density sensor array will have at least about 400 electrodes, though electrode arrays as considerably higher may be obtained and are also contemplated herein.

An analog-to-digital converter coupled to each of the electrodes generates a digital signal as a function of the electrical potential detected by the electrode means, which is processed by means coupled to the analog-to-digital converter for generating an output signal as a function of the digital signal.

The cells of clinical interest may be associated with any state, status, or condition that creates the necessary electrical potential. Such conditions include fibrocystic disease, cancer, tissue damage, inflammation, and changes associated with reproductive processes. For instance, the apparatus may be used with cancers such as breast cancer, testicular cancer, liver cancer and lung cancer.

The apparatus may also be used with tissue damage that is a continuing process which results from ongoing connective tissue disorders, or for detecting the electrical potential differences brought on by the healing of tissue damage, such as soft tissue healing or bone healing.

The apparatus may also find use in detecting the electrical potential of inflammatory processes responding to an infection.

The apparatus may also be used in detecting the electrical potential of the reproductive process in fetal development, or, alternatively, in assessing the state of follicular rupture in ovulation.

In a preferred use of the apparatus, the array is placed over a portion of an external surface of the living organism, though in other embodiments it may be adapted for placement over a portion of an internal surface of the living organism.

A preferred construction for the electrode array comprises a non-conductive material conformable to the surface having the electrodes spaced therein, for instance where the material is contoured to the shape of the surface. In another preferred embodiment, the conformable material flexes over the surface.

In an alternative embodiment the array is formed from at least two interlocking units. These units may be articulated to be positionable to maintain substantially all of the electrodes in electrical contact over a non-planar surface of the living organism.

In one preferred embodiment the electrodes are spaced regularly in the array, though they may also be advantageously spaced in a pattern designed to match a particular clinical application.

A conductive material is in contact with the surface, and the conductive material has an ionic content optimized for a stable signal connection to the surface. Preferably, the ionic content is optimized to approximate the surface ionic content.

In a preferred apparatus the conductive material is a stabilized conductive medium, more preferably a medium that contains water, such as a gel.

The electrodes are preferably formed in the non-conductive material by a printing process from a conductive polymer based ink. The conductive ink may be a silver/silver chloride, or other metal/metal chloride. The electrodes also preferably are connected to electrically conductive trace lines, which preferably are formed from a similar conductive polymer based ink by the same printing process.

In a further preferred embodiment, the electrically conductive trace lines run along an extension of the non-conductive material, and away from the plurality of electrodes.

The apparatus further may comprise a housing for securing to the extension, and having electrical connections spaced to match the spacing of the trace lines along the extension of the non-conductive material, such as by a series of conductive filaments oriented perpendicular to the trace lines when the connector is mated to the extension. The housing may be secured by any of conventional means, such as slotted and mated connectors, or clamping.

The invention also provides a method for assessing the clinical significance of array readings of a living organism, the method comprising the steps of: (a) taking a set of measurements of the electrical potential of each electrode of an array at a first surface overlying a site containing cells of clinical interest; (b) taking the measurement of the electrical potential of at least one other surface of said living organism as a reference at the same time as the measurement in step (a); (c) determining the variability of measurements of the array electrodes; (d) setting a normal control for patient mean values across the array; (e) measuring the variability of signals; (f) performing a convolution of each measurement at each location of the array, by averaging each array measurement with itself and its nearest neighbors, thereby generating a new set of array values; (g) repeating steps (b) through (f) at least three times, using the previous convoluted values as the starting measurement value for each subsequent step; (h) adding the differences over the array value convolution step to get an index number for the differential value corresponding to the variability of measurements of the array; and (i) assessing the clinical significance of the array readings based on the number obtained in (h).

One preferred method uses a high-density sensor array having a density of at least about 9 electrodes per square inch.

In a second preferred method, a second site is also measured, preferably by taking a set of measurements of the electrical potential of each electrode of an array at a second surface overlying an anatomically equivalent surface to the first surface. The anatomically equivalent second surface is preferably a bilaterally symmetrical surface equivalent of the organism. In an alternative preferred method, the anatomically equivalent surface is the same surface measured over time.

In a further preferred method, the surfaces are equivalent surfaces of each breast of a human subject and the clinical significance is the presence or absence of a condition of abnormal cell growth, such as cancer.

In another further preferred embodiment, the step in (g) is repeated at least about 4 times, more 6 times, and even more preferably at least about 8 times.

By step (i), the method is preferably practiced by selecting clinical significance levels for the numbers in (h) that creates a minimal number of diagnostic false negatives. Preferably, the false negative rate is equivalent to the false negative rate resulting from biopsy assessment, on the order of less than 1%.

In another preferred embodiment, the method excludes at least about 30% of biopsy candidates as benign, more preferably at least about 50% of candidates and most preferably excludes at least about 70% of candidates as benign.

In addition to measuring differences in surface electrical potentials between various areas of a surface of the body at a particular time, the present invention allows physiological changes in a single area of interest to be visualized and monitored over a period of time. Because of the high density of the array, it reduces the granularity of the data (similar to increasing the number of pixels in an image), and allows a display of the physiological changes in the tissue within the area of clinical interest.

BRIEF DESCRIPTION OF THE DRAWINGS

FIG. 3 are planar views of alternative shapes of the high-density sensor array.

FIG. 4 is a planar view of a further alternative embodiment of the high-density sensor array.

FIG. 7 is a block diagram for the production of the high-density sensor array.

DETAILED DESCRIPTION OF THE INVENTION

Figure 1:
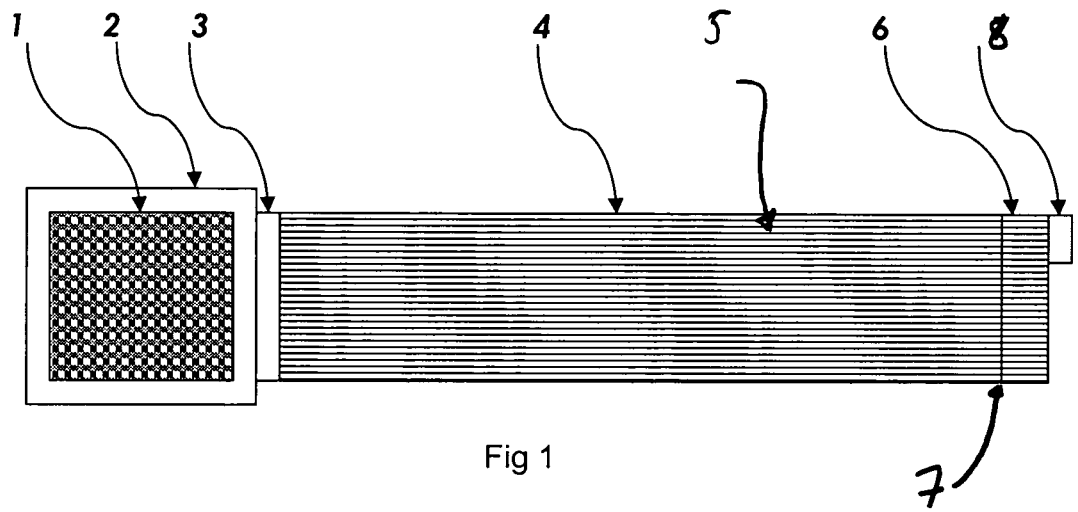
FIG. 1 is a planar view of the high-density sensor array.

FIG. 1 is a planar view of the apparatus of the invention, a high-density sensor array, for assessing the electrical potential of cells in a living organism of clinical interest.

Many cases exist where a cell or group of cells has an altered electrical potential, including occasional, though normal, states of cells such as gestation or healing, as well as abnormal or anomalous growth states or conditions, including disease or malignancy. In this sense, the physiologic state of cells of the organism can be evaluated by assessing the electrical potential of the cells.

Examples of such conditions include fibrocystic disease, cancer, tissue damage, inflammation, and changes associated with reproductive processes. The apparatus is particularly well-suited to be used with many types of abnormal cells (including cancer cells) with potentials markedly different from normal cells. Malignant cells and normal cells have different membrane permeabilities which in turn affects the electric potential across the membrane. Typically, the difference between normal cells and malignant cells is 20 mV or greater.

Anatomically equivalent surfaces are chosen, i.e., equivalent in being a bilaterally symmetrical surface equivalent of the organism. Alternatively, the anatomically equivalent surface is the same surface measured at a different time. In the case of breast cancer, the surfaces are co-planar surfaces of the chest of a human subject, as in the equivalent surfaces of each breast Transmembrane electrical potentials arise from differences in ion gradient across a plasma membrane. Animal cells have a characteristic profile of ion gradients across the plasma membrane under steady-state conditions. An altered electrical potential can exist for any cellular state, status, or condition that creates the necessary electrical potential difference for detection by the high-density sensor array.

The method is based on the detection of aggregate differences of transmembrane potentials among varied cellular states. These differentials can be detected from the skin surface, thus it is also referred to as the difference in surface electrical potentials, or electrical potentials.

In the case of breast cancer, there are two main events that give rise to a detectable signal, rapid mitotic changes in cancerous lesions and structural changes in breast ducts.

During the process of mitosis, transmembrane potentials change from −70 mV to −20 mV. Normal cell division goes on in both breasts, and therefore cancels out. When compared with normal tissue, rapidly growing cancers demonstrate a very the high rate of cellular division, which results in significant, localized changes in skin surface electrical potentials, readily detectable by the high-density sensor array.

As to structural changes in the breast ducts, the ducts are lined with endothelial cells that have a distinct polarity. The luminal membrane of the cell has a transmembrane potential of −70 mV. The basilar membrane has a transmembrane potential of −100 mV. This difference in potential is maintained by the cellular metabolic pumps that maintain the differing ionic concentrations in the luminal and basilar regions. "Tight junctions" between adjacent cells of breast ducts prevent ions from diffusing and aid in maintaining of polarity.

In cancer, the disorganized cell growth and division results in the chaotic arrangement of the cells, which lacks the orderly formation of the "tight junctions". Hence, electrolyte can diffuse between luminal and basilar cell areas, bypassing its metabolic pumps. This diffusion produces localized changes in ionic distribution and differing cell membrane potentials in cancerous ducts when compared to non-cancerous ducts. Detection of the resulting surface electrical potentials by high-density sensor array may indicate the presence of ductal carcinoma in situ (DCIS), improving the detection of this hard-to-diagnose type of cancer. Other cancers, testicular cancer, liver cancer and lung cancer, for example, will have similar altered electrical potentials. In other cases, the differences may relate to the fact that tumors frequently outgrow their blood supply, resulting in areas of necrosis, often developing necrotic centers.

Other applications may include detecting the anomalous conditions of cells where the measurement involves such practices as monitoring of the response to chemotherapy, monitoring of members of a high-risk (e.g., genetically predisposed) population, measuring inflammatory processes and their response to treatment, organ regeneration, and wound healing processes.

In other situations, the high-density sensor array may be used with tissue damage that is a continuing process which results from ongoing connective tissue disorders, as in certain autoimmune disorders, or for detecting the electrical potential differences brought on by the healing of tissue damage, such as soft tissue healing or bone healing.

Looking to FIG. 1, the high-density sensor array has a main or central patient interface region 1 with silver-silver chloride electrodes with hydrogel electrolyte caps formed therein, an adhesive outer ring 2, a further adhesive strain relief 3, and a connector tail extension, or tail, 4 with double sided printed conductive connection traces 5 from each electrode to the connector end of the array 6. The printed line 7 is used to indicate that the array tail has been fully inserted into the connector housing, and the connector tab 8 ensures that the tail is inserted correctly and fully into the connector.

While the drawings depict the electrodes formed within the patient interface as having a generally round configuration, in some cases alternative shapes may be desired. For instance, triangular shaped electrodes can be arranged at a higher electrode density, while maintaining a constant area for each electrode. It may also be sized for use in different applications.

The high-density sensor is a single-use, disposable product applied to an area of interest in a manner similar to a nicotine skin patch. The diagnostic outputs are based on algorithms. The high-density sensor array procedure is electrically passive, thus safe for patients. With the high-density sensor arrays, test results are available immediately after a procedure, and multiple repetitions of the procedure are feasible for patients in high risk categories without electromagnetic field (EMF) exposure or even minimally-invasive surgical procedures. This will result in improved patient morale and increased physical comfort.

Figure 2:
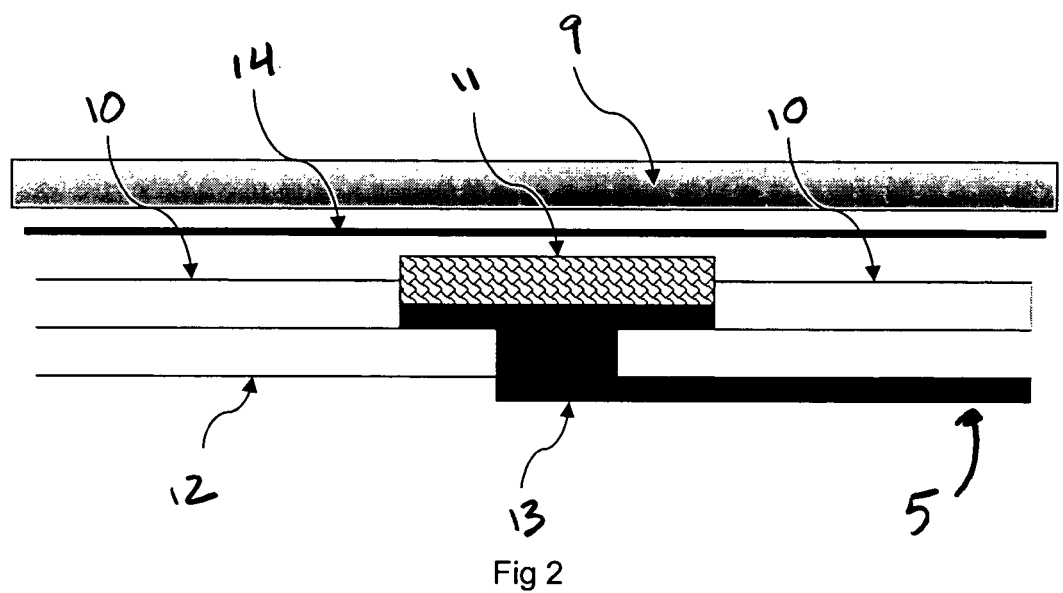
FIG. 2 is a side view of the high-density sensor array, showing an electrode sensor.

For a good connection of the electrodes of the patient interface to the patient, the high-density sensor array must include an adhesive system to insure good skin contact, an electrolyte, an electrolyte confinement system to prevent contact between adjacent electrodes, and an electrode that creates the contact with the external measurement system. FIG. 2 is a side view of the high-density sensor array illustrating the construction of an individual electrode 13 and its application to a subject surface 9, for instance, an patient's skin. The high-density sensor array includes an adhesive system 10 to maintain close contact with the skin 9, a hydrogel 11 formulated to achieve rapid stabilization with the skin chemistry, a flexible nonconductive substrate 12, and a printed electrode 13 and trace 5 based upon a silver-silver chloride conductive material. A release paper covering 14 would be left in place to protect the adhesive and hydrogel until such time as it was removed to apply the array to the patient's skin 9. For illustrative purposes FIG. 2 shows the trace on the back side of the substrate. The conductive traces 5 that link each electrode to the end of the connector tail can be produced on either side of the substrate 12, in FIG. 2 this is on the side away from application to the subject skin 9.

The patient interface construction of the high-density sensor array provides many advantages over using numerous smaller-sized individual sensors, and even if one were to use many more smaller individual sensors, many of the economic and human factors problems would remain, for both medical providers and patients. For example, using additional pairs or sets of electrodes would substantially increase the amount of clinical time and resources consumed per test. Additionally, there would be difficult measurement problems involving individual electrode settling times given the low DC microvoltages being measured.

The use of printable conductive inks allows for the creation of much higher densities of electrodes, which provides greater physiological process visualization, with improved feature extraction algorithms. In addition, the printed arrays provide superior patient fit and rapid, uniform signal stabilization.

FIG. 3 shows planar views of several alternative shapes of the high-density sensor array. The geometry of the high-density sensor array is only limited by the need to facilitate an effective conformation of the array with the skin surface. To that end, the various array geometries will be used to enhance the ability of the high-density sensor array to conform to the curvature of the surface for particular applications.

The electrodes 13 of the high-density sensor array are connected to electrically conductive trace lines 5, which may be formed by the same metal/metal chloride polymer based ink by the same printing process. As seen in FIG. 1, the electrically conductive trace lines 5 run along an extension 4 of the non-conductive material, and away from the plurality of electrodes.

The flexible substrate 12 can be made of various materials including plastic, gel, cloth, paper, or hybrid materials, with the electrodes applied to the substrate in various ways known to the industry.

The high-density sensor array has a density of at least about nine electrodes per square inch. For a four square inch patient interface, the total number of electrodes would be thirty-six. Higher densities may be advantageously utilized, for instance densities of at least about twenty-five electrodes per square inch, which, when used in a four square arrangement would provide 100 total electrodes. A ten square electrode arrangement would provide a density of about 100 electrodes per square inch, providing 400 electrodes in a four square inch high-density sensor array.

With advanced manufacturing technologies, high-density sensor arrays that are even higher may be advantageously employed, limited only by the necessity of the adjustments made to the algorithms and other features of the device, including design features to provide the density and connections of the electrodes to the measuring device.

The electrodes are spaced regularly in the array in FIG. 1, though they may also be advantageously spaced in a pattern designed to match a particular clinical application, for instance, with a pattern or geometry uniquely designed to measure a particular internal structure, such as an organ, beneath the surface 9. The electrodes can also be altered in size, either uniformly larger or smaller, or varying in size.

The high-density sensor array is placed over a portion of an external surface of the living organism. In alternative embodiments it may be adapted for placement over a portion of an internal surface of the living organism.

The high-density sensor array comprises a non-conductive material conformable to the surface having the electrodes spaced therein, for instance where the material is contoured to the shape of the surface. The conformable material is preferably a material that will flex over the surface.

The patient interface portion 1 can have any shape permitting a uniform distribution of sensors over the area of interest, and that insures reliable skin contact for measuring the required electrophysiological data. Configurations of high-density sensor arrays for particular applications will vary, and can be optimized for conformation to various sizes of surfaces to be measured. The array connector length and placement, aggressiveness of the adhesive system, coverage area, and electrode density will also vary, depending on the target patient population and application for the high-density sensor array.

As seen in FIG. 3, and depending upon the application, the patient interface portion 1 may have a rectangular, conic, or even geometric profile, though it will typically retain a long connection tail extension 4 of the same flexible substrate. The patient interface portion 1 can be of different sizes or even trimable to be sized to fit particular applications.

With reference to FIG. 4, the high-density sensor array may be adjustable for use with a particular patient body type or area of the anatomy, such as by cutting along a line 15 printed on the patient interface portion 1. This array maintains the features of an adhesive wing 16, with adhesive strain relief 17, the conductive traces 5 with an insertion depth line 7 and an index tab 8. In this embodiment, a certain category of traces linked to the excluded array region will provide no signal, which the computational device will recognize as indicating the reduction along line 15 was made, allowing for compensation in the analysis to include only the electrodes of the remaining region.

Figure 5:
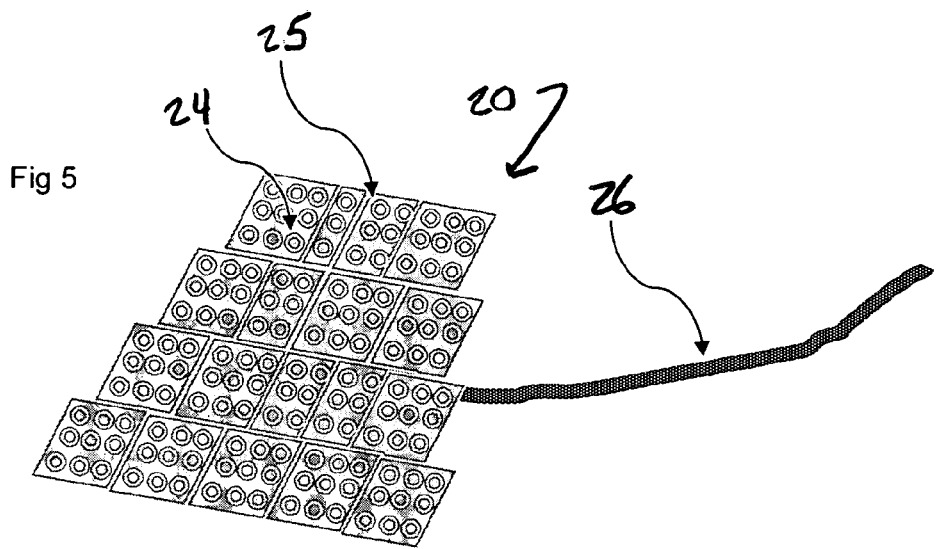
FIG. 5 is a planar view of a flexible embodiment for the high-density sensor array.
Figure 6:
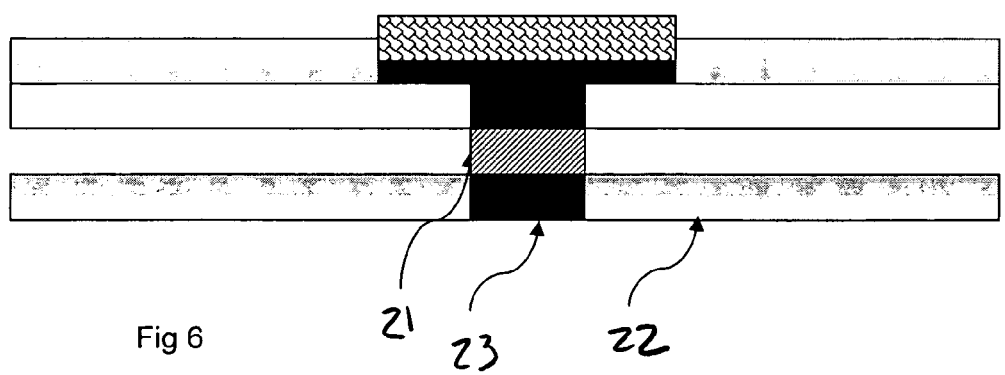
FIG. 6 is a side view of a different embodiment of the sensor electrode of the high-density sensor array.

FIGS. 5 and 6 relate to a different embodiment of the array, a flexible design 20 (FIG. 5). Here the array is fabricated as in FIG. 1, but there is no conductive trace on the back side of the substrate and no tail. As seen in reference to FIG. 6, an electrical connection to the electrodes on the upper surface is made by placing a dot of conductive adhesive 21 on the back side in contact with the feed through. The high-density sensor array is then placed on a reusable flexible backing plate 22. At regular intervals a conductive contact point 23 passes through the backing plate 22. The arrangement and density of these contact points are chosen and selected on the same basis as that used for the array. The flexible array 20 is embossed in a pattern to register the array to the backing plate system which is comprised of a number of interconnected plates (subunits) that permit it to flex to conform to curved surfaces, as shown in FIG. 5.

The high-density sensor array may be formed from at least two interlocking units. These units may be articulated to be positionable to maintain substantially all of the electrodes in electrical contact over a non-planar surface of the living organism. This flexible design 20 has multiple interlocking, flexible flat subunits 24 with a uniform placement of conductive contacts to register and mate with the conductive adhesive on the back of the tailless disposable arrays. The number of subunits is based on the desirable geometry under measure. This backing plate has numerous flexible joints 25 where each of the subunits is connected to the adjacent subunits. The conductive contact points on the subunits 25 are connected to a wiring harness 26 that connects to a user chosen analog to digital (A/D) processing system.

FIG. 7 is a block diagram showing the steps that are taken in the production of a typical embodiment of the high-density sensor array. This production may be applied to any of the embodiments.

In this method, the high-density sensor array is produced by perforating the substrate at feed through locations, and then applying conductive material at the same feed through locations. To the upper surface is applied a silver-silver chloride conductive material forming electrode lands and conductive traces to the connector end of the tail. Applied to either the back side, or both front and back, is conductive material forming conductive traces from the electrode feed to the connector end of the tail. An adhesive material, for instance an adhesive film, is then applied to the top surface outlining the electrode lands and forming the adhesive edge and strain relief noted in FIG. 1.

Disks of hydrogel are placed on top of each electrode land, and finally, a release material, for instance, a die cut release paper, is applied over the adhesive area to seal in an air-tight package for each electrode.

Conductive inks are used widely in various electronic mechanisms (i.e. anti-counterfeiting devices on security instruments). In the high-density sensor array, deep-cup electrodes of prior art devices are replaced with spots of such conductive printable inks. The electrodes thus formed on the non-conductive material by a printing process from a metal/metal chloride polymer based ink, such as a silver/silver chloride ink. Printable conductive inks also form the conductive traces, or "wires", connecting the electrodes to the detection mechanism. Printable inks enable an increase in the density of the array (number of electrodes per square inch) to improve data resolution and to decrease overall weight of the array.

In the course of manufacture, the hydrogel is placed directly on top of the printed silver/silver chloride ink electrodes. The area around each hydrogel island is then isolated by the adhesive. The method of manufacture for the high-density sensor creates electrodes that are as close to chemically identical as possible, which helps to maintain uniform signal integrity.

The sensor electrodes are used to detect the potential of the static and quasi-static electromagnetic fields of the groups of cells proximal to each electrode. The array is placed overlying at least a portion of a surface of a living organism, such as the human breast, overlying a site suspected of containing cells of the anomalous condition, in such a fashion that substantially all of the electrodes are electrically contactable with the surface. The high-density sensor array utilizes passive electrodes, and can be connected to a source capable of monitoring the electrode integrity.

Figure 8:
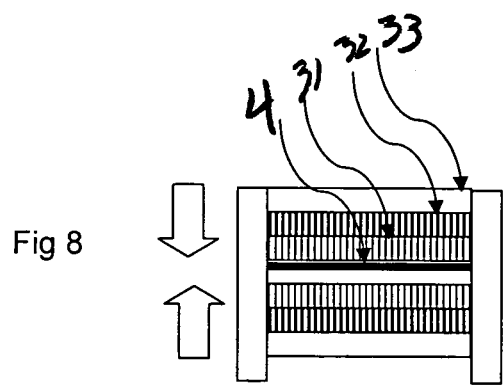
FIG. 8 is an end view of the connector for the high-density sensor array.
Figure 9:
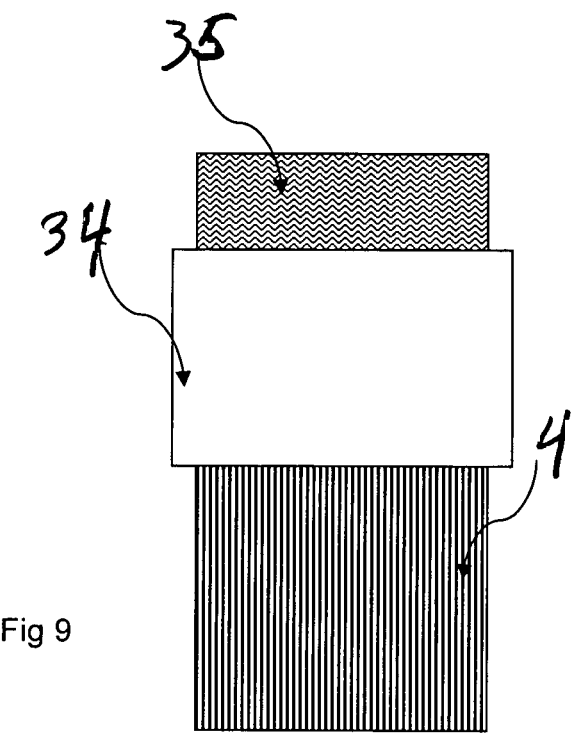
FIG. 9 is a top view of the connector for the high-density sensor array.

The high-density sensor array further may comprise a housing having electrical connections spaced to match the spacing of the trace lines along the extension of the non-conductive material, such as by a series of conductive filaments oriented perpendicular to the trace lines when the connector is mated to the extension. FIG. 8 and FIG. 9 are pictorial descriptions of a clamping connector that mates with the array tail and tab. This connector functions similarly to a zero insertion force socket well known to the industry.

FIG. 8 is an end view of the connector. The large arrows to the left indicate the closure of the clamp. The clamp consists of a functionally identical upper and lower assembly. The tail of the high-density sensor array 4 is inserted fully into the clamp. Both the upper and lower components of the clamp are constructed as follows. A vertically conductive polymer sheet 31 makes the contact with the conductive traces on the array tail 4 and the conductive traces on the PC board 32 in the connector. The traces on the PC board are spaced to match those on the array tail. The conductive polymer sheet is a commercial product having vertically embedded (perpendicular the surface of the sheet) conductive metal fibers in a nonconductive polymer matrix. This results in a material that will conduct electricity vertically through the sheet but not laterally. The PC board is supported by a backing plate 33 completing that half of the connector.

FIG. 9 is a top view of the connector showing the array tail 4 inserted into the connector body 34 and the wiring harness 35 for the connector.

Connecting the on-screen interface to the hardware and its input devices is equally important, as is the display and the organization of a patient management data about the procedure. Electrode integrity testing is incorporated as a part of this hardware design.

The degree of flexibility and the density of the array are controlled depending on the specifications for a particular application. In each case, the finished array design will have ease of use, accuracy, an array of useful data collected, and overall design methodology optimized for the application, and to address functional concerns, such as the positioning of sensor arrays, cable management and connectors, and the location of peripheral functions such as printing and calibration.

The conductive material is placed in contact with the surface. The conductive material has an ionic content optimized for a stable signal connection to the surface. Preferably, the ionic content is optimized to approximate the surface ionic content.

In a preferred high-density sensor array the conductive material is a stabilized conductive medium, more preferably a medium that contains water, such as a gel. The high-density sensor array system measures essentially constant electrical potentials. In case of high-density sensor array, the source of the baseline drift is due to the ionic currents that result from the movement of the ions in the synthetic electrolyte in the electrode itself and in the natural electrolytes on the surface of the skin. As diffusion of ions takes place, changes in potential occur. Elimination or minimization of baseline drift is essential for correct measurements. The electrolyte/electrode material combination must achieve rapid stabilization on contact with the skin.

In the use of such electrodes, a complex battery is formed consisting of many interactive components including the electrode material (frequently silver/silver chloride), the electrode gel, internal body chemistry and external skin conditions, skin preparation, temperature, air condition and chemistry, etc. Obviously, some of these factors are not subject to control, but in order to get the best data possible, especially in instances where DC electrical potentials are of interest, artifacts, such as DC offsets, should be reduced to the lowest level. Therefore, the hydrogels should have a rapid stabilization time. Most of the biomedical electrodes, such as disposable electrocardiogram (ECG) electrodes, measure a changing signal, and will show drift, i.e., one would see the baseline wander over time.

The traces from the electrodes are connected to the A/D converters either directly or preferably through a set of multiplexers that permit each A/D channel to be connected in sequence to a number of electrodes. As the signals of interest are essentially constant, the small intervals between measurements (milliseconds) will have no impact on the validity or comparability of the measurements. Such devices are well-known to the art for splitting signals to a computational device originating from multiple data sources.

The high-density sensor array system includes an analog-to-digital converter coupled to each of the electrodes of the patient interface to generate a digital signal as a function of the electrical potential detected by the electrodes, which is processed by means coupled to the analog-to-digital converter for generating an output signal as a function of the digital signal.

Figure 12:
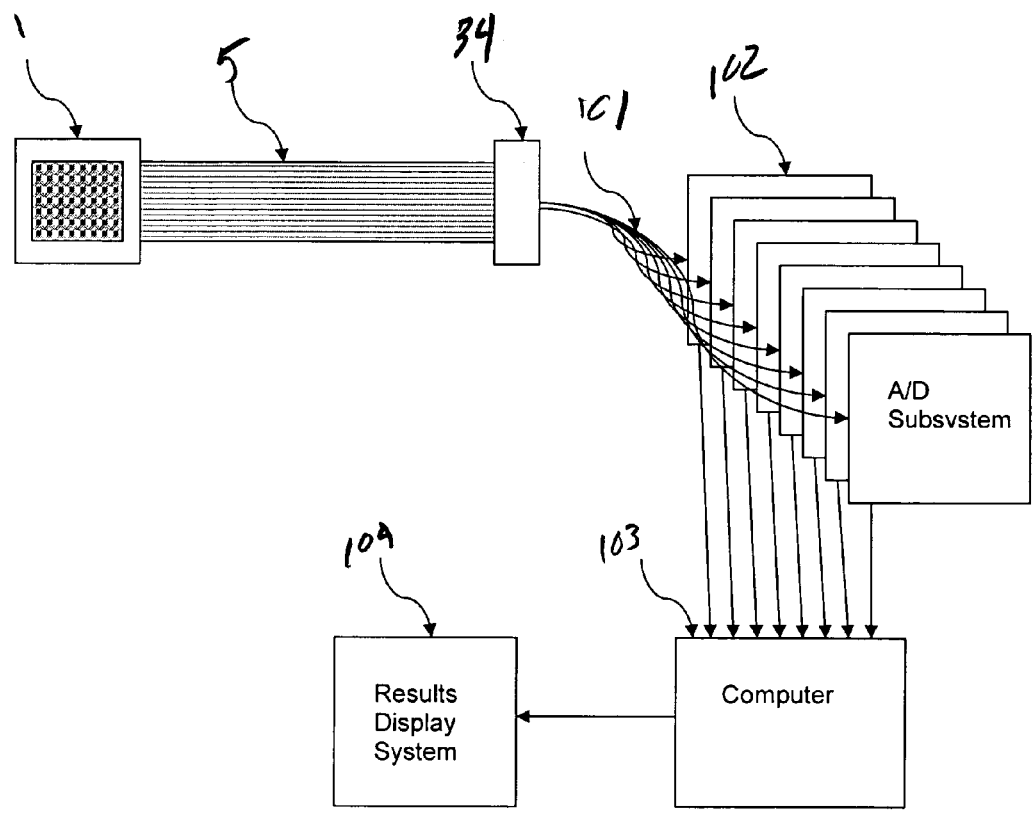
FIG. 12 is a block diagram of a typical embodiment showing all of the components in the system.

FIG. 12 is a block diagram of a typical arrangement for the high-density sensor array system. The system includes the array of electrodes formed as the patient interface for making contact with the subject, with the "tail" section of the array that incorporates the conductive traces 5 to the electrodes. A trace line mating connector that connects to the tail section of the array system 34 has a cable 101 from the trace line mating connector that transfers the analog signals from the electrodes to the A/D subsystems 102. The A/D subsystems 102 are where the analog signals are sequentially transformed into their digital equivalents and passed on to the computer 103 for processing. Multiple A/D subsystems 102 are used to achieve the required number of input channels (one for each electrode in the array 1). In the computer 103 the algorithm is applied to the digital signals. Finally, there is a display system 104 used to present the real time outputs of the algorithm to the use in various clinically relevant formats.

Figure 13:
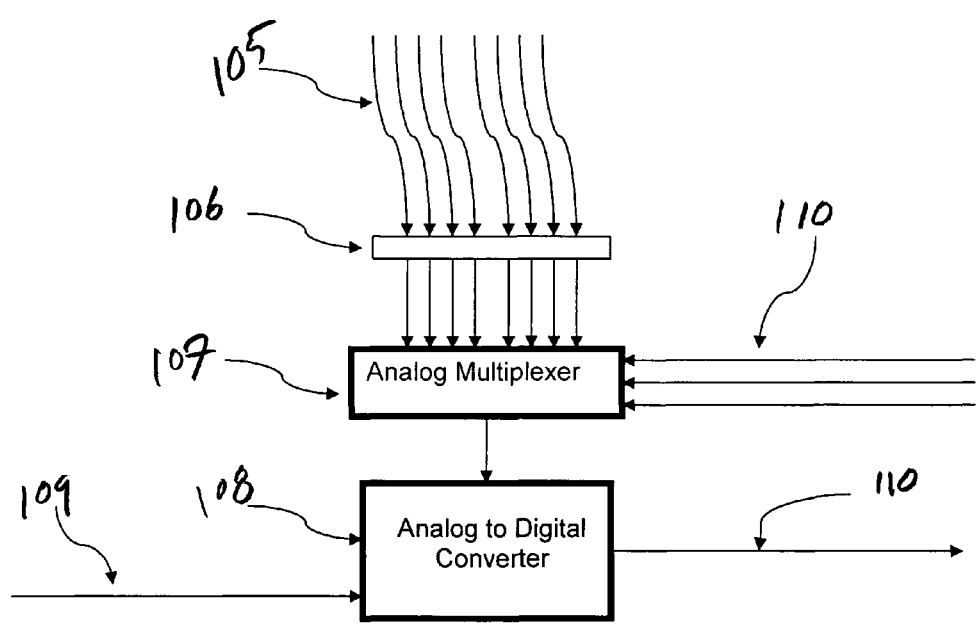
FIG. 13 is a block diagram of typical A/D subsystem of FIG. 10.

FIG. 13 provides a more detailed consideration of the elements of a typical A/D subsystem shown in FIG. 12. In FIG. 13, a subset of the wires 105 from the clamping connector (in this example 8 wires) connects to a connector 106 for the wires on the printed circuit board that houses the components of the A/D subsystem. An analog multiplexer 107 that permits the selection of an individual signal from one of the wires connects then to the A/D converter 108 that acts on the signal selected and converts it to its digital equivalent. Connection to the reference electrode(s) 109. Digital connections from the computer 110 specify which of the analog signals entering the multiplexer is to be passed to the A/D converter 110, and a digital connection from the A/D converter 108 passes the digital value to the computer for processing.

This type of embodiment, incorporating multiple A/D subsystems is typically used when large numbers of analog signals must be managed. Given that all of the analog to digital converters must function identically to preserve comparability of the data it is desirable to use as few as possible. Hence, using multiplexers reduces the total number of A/D converters that must be used. Multiplexers are available with many different input capabilities (4, 8, and 16 channel devices are readily available). The actual type of multiplexer utilized and number of subsystems required will be dependent on the number of electrodes that must be analyzed.

The diagnostic algorithm used in the high-density sensor array device is based upon the comparison of differences in electrical potentials measured from the surface of the breasts. The algorithm is based on the comparison between the electrodes within each sensor array. The index averages signals with minor differences from their immediate neighbors and amplifies signals with differences greater than the normal signal noise. In essence, the algorithm is an extraction process that reduces the background noise while amplifying signal of interest. Extraction processes are commonly used in image processing programs, where improvement in signal-to-noise ratio is required (i.e. computerized tomography).

After taking an array of measurements of a physiologic state of cells of an organism at a surface area overlaying the cells of clinical interest, the differences among the electrodes are evaluated through a convolution applied to each electrode reading wherein the value of the electrode reading is adjusted to reflect those of its nearest electrodes. When using comparable anatomical sites, the variability of measurements is first determined at each of the surface areas underlying the respective high-density sensor arrays separately, setting a normal control for patient mean values across both surface areas, and measuring the variability of signals between each of the surface areas.

Whenever the array is a regular rectangular array there will be eight adjacent electrodes to any given electrode. Hence, a 3 by 3 convolution can be applied. Should a hexagonal or pentagonal or other arrangement be utilized a convolution similar to that geometry would be applied. In any case, the convolution weights the values of the electrode of interest and its adjacent electrodes and produces a new value for that electrode. This step has the effect of removing minor variations between electrodes while preserving major variations. By averaging each electrode measurement with itself and its nearest neighbors, a new set of array values is essentially generated.

Next, an average for the array is computed and the sum of the differences from average is computed. This step provides a measure of the variance, either within an array, or between different arrays. An advantage of utilizing duplicate high-density sensor arrays on both an affected and unaffected region is that in some cases the regional variation may be great, while the differences between regions is small, on the order of about 8 mV. When the algorithm is applied, the variations between regions can remain small, even for repeated applications of the algorithm. However, in a patient with a cancerous lesion, the algorithm values will be markedly different within the affected region.

In either case, the convolution process is repeated at least three times; adding the differences over each array value convolution step to get an index number for the differential value corresponding to the variability of measurements of the arrays; and assessing the clinical significance of the array readings based on the number obtained. In a further preferred embodiment, convolution can be repeated at least about 4 times, more 6 times, and even more preferably at least about 8 times.

The resulting numbers form a basic index. Normal tissues produce low numbers while cancerous tissues produce higher numbers.

The absolute measurements algorithms of prior art methods do not take into account the variations seen in the normal population. The variation in the normal population can be related to a number of issues, including the absolute magnitude of the average signal, the distribution of electrical potentials across the surface of the skin, pregnancy, and a history of non cancerous breast tissue changes.

It has been found that the signal strength of subjects with a normal medical history is relatively constant across all parts of the breast surface. However, a greater degree of randomness in the signals is found in subjects with a history of benign fibrocystic disease. This problem could not be resolved by the prior art diagnostic algorithms, as previous techniques used algorithms that rely upon the subtraction of the values of readings taken in the same relative position on both breasts from a limited number of electrodes. Positional differences in electrode and individual patient variation can adversely impact the accuracy of such an algorithm. Relying solely on average values can not correct for these problems.

The use of a high-density sensor array, and the method utilizing the algorithm, takes into consideration population variability, as well as variability within single breast.

Figure 10:
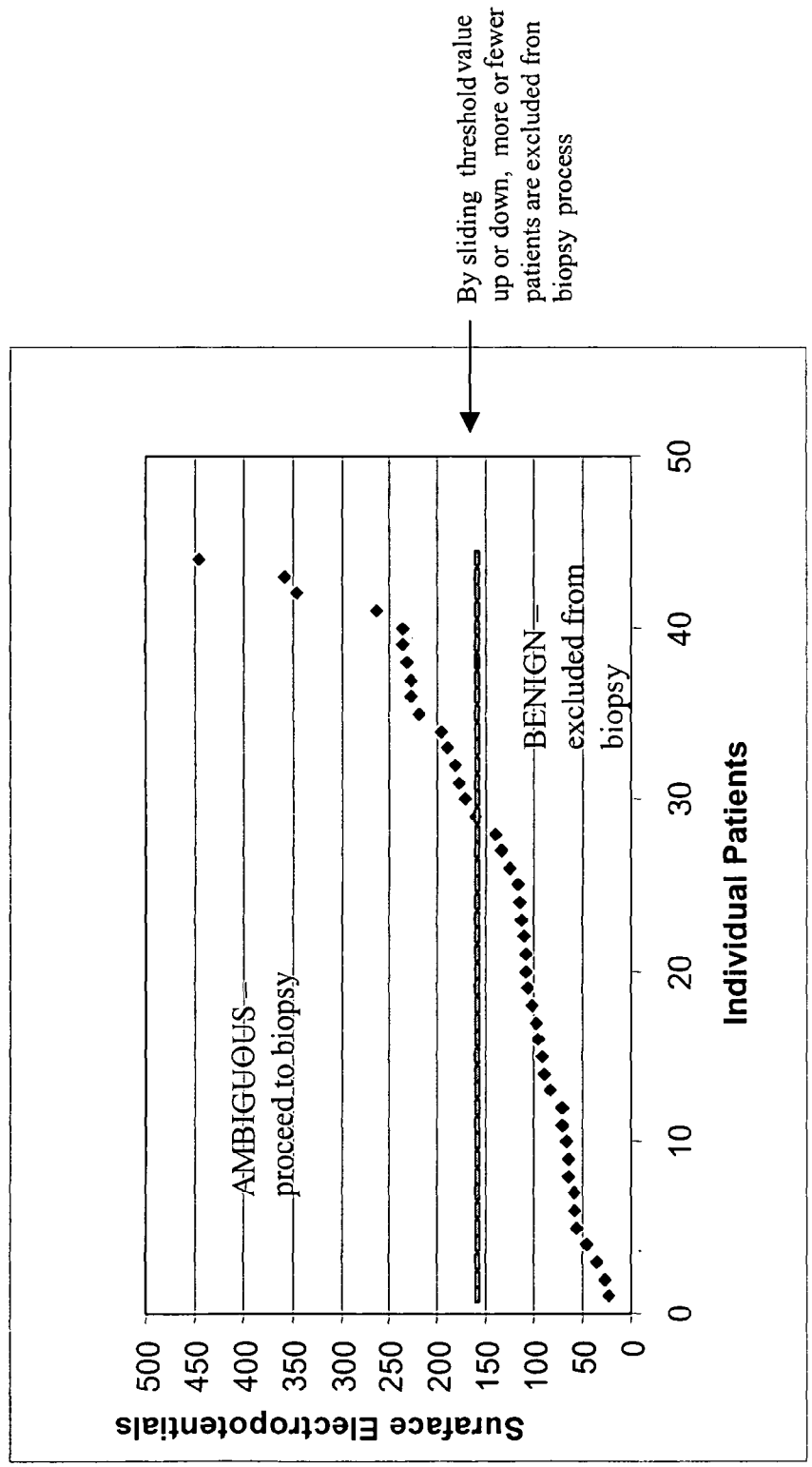
FIG. 10 is a view of graphed data obtained by the invention, demonstrating a first alternative cutoff made for further biopsy procedure.
Figure 11:
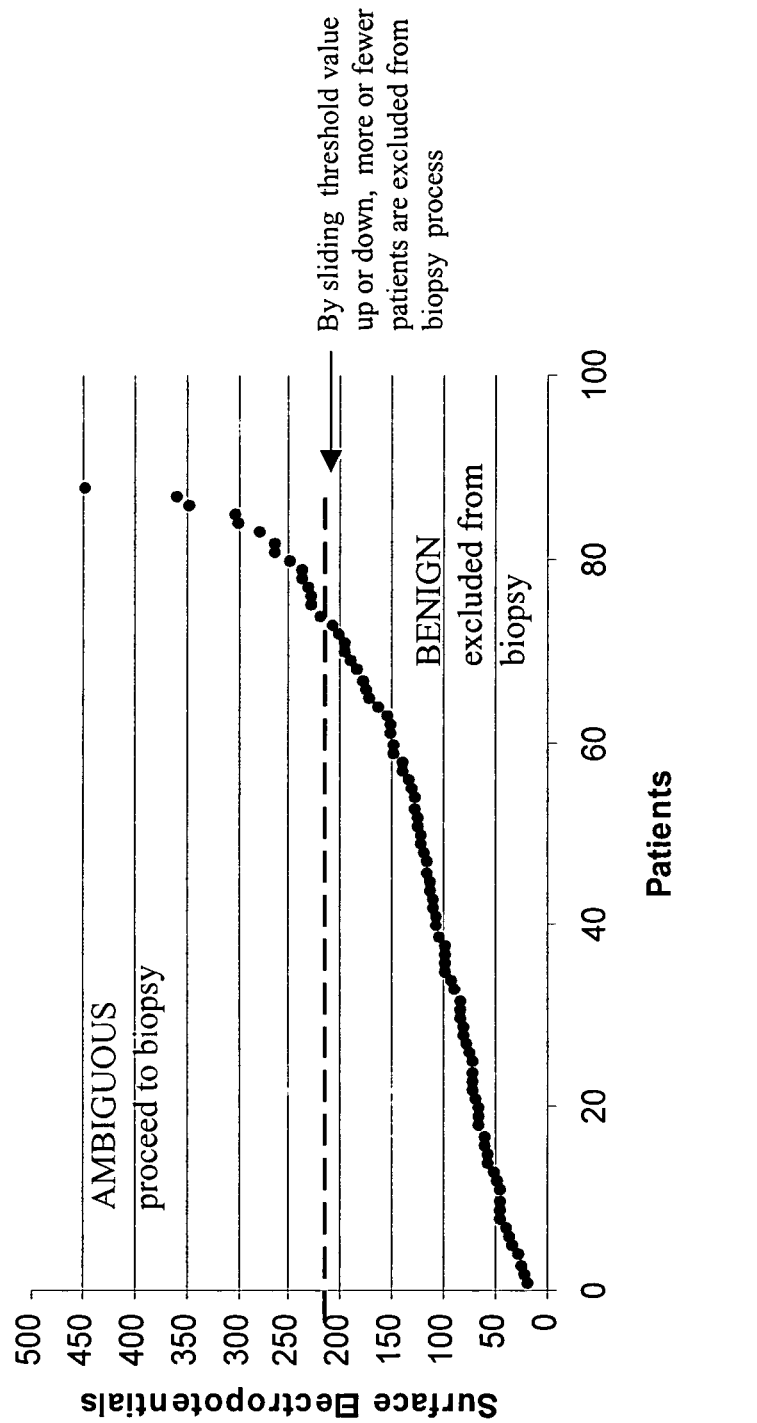
FIG. 11 is a view of graphed data demonstrating a second alternative cut.

The threshold values determine the percentage of patients excluded from the biopsy process. By lowering these values, more patients are sent to biopsy, decreasing the number of false-negatives. This is demonstrated in reference to FIGS. 10 and 11, by sliding threshold value up or down, more or fewer patients are excluded from the biopsy process. This selection must be made mindful that the more patients that are eliminated from biopsy processes, the higher the risk of excluding some patients with true cancers.

It must also be remembered that differing numbers of electrodes and weighting factors will produce different absolute values for the index. In every case, however, the use of the algorithm for feature extraction will produce noticeable differences in the final index values for cancerous vs. normal tissue. With the high-density sensor array apparatus and method, it will be possible in the future to exclude 70% of patients from the biopsy process, with less than a 1% false negative result, though if it were desirable to have an even lower false negative level, even excluding 50%, or even as little as 30% of biopsies would result in considerable healthcare savings and more effective patient management.

When the high-density sensor array system is used to exclude patients from the biopsy process, it can follow either screening mammogram procedures, in the case of non-palpable lesions, or physical identifications of suspected masses, in case of palpable lesions. The present device and method reduces the number of patients sent for biopsy by accurately identifying benign tissues, with less than a 1% false-negative rate (which is comparable with the currently accepted false-negative rate of biopsies).

High-density sensor arrays provide expanded coverage of tumor types and increased accuracy as compared with diagnostic mammography. Other diagnostic technologies, for instance high definition ultrasound (HDU) and magnetic resonance imaging (MRI), may be used in parallel with sensor arrays, as fine-tuning filters for analyzing very specific types of tissue structures.

In addition to measuring differences in surface electrical potentials between various areas on the surface of the body at a particular time, a single area can be studied with the high density array over a period on time. This process can disclose changes in the tissues under the area of interest. This is particularly beneficial in the management of patients on chemotherapy drugs. Given the toxicity of these drugs, measuring the response of the tumor being treated will permit rapid appropriate modifications of therapy if the tumor activity measured by the high density array over a period of days does not show the desired response to the drug. The dosage can be changed or that drug discontinued and a different chemotherapy agent used.

Similarly, bone healing rates can be assessed by utilizing the high density array to monitor the surface electrical potentials characteristic of bone healing over a period of weeks. Further, tissue healing can also be monitored by the high density array over a period of days. This has a significant potential as an adjunct to laproscopic surgery where the incision site is remote from the actual area of surgery.

The sensor array allows the quick clinical application to patients of very high density multiple electrodes with specialized uniform physiochemical characteristics, and reproducible inter-electrode spacing. After the array is applied to the patient, the low level electrical potential signals are fed to standard A/D converters for conversion to digital formats and on to a computer for processing and analysis in real time.

The high-density sensor array permits the taking of electrical potential measurements and analyzing such measurements to provide assessment of various cellular states, including monitoring of healing or tracking the course of treatment or disease, diagnosis and screening of disease, such as providing an indication of anomalous cellular condition in a living organism, and eliminates the limitations of previous devices and methods. It is safe for patients, is simple and quick to use, conforms to varying topologies, and can be mass produced inexpensively in order for high quality clinical analysis to be cost effectively performed.

While there have been shown and described what are at present considered to be the preferred embodiments of the present invention, modifications thereto will readily occur to those skilled in the art. It is not desired, therefore, that the invention be limited to the specific arrangements shown and described, and it is intended to cover in the appended claims all such modifications as fall within the true spirit and scope of the invention.

What is claimed is:

1. A system for assessing the clinically significant electrical potential created by static and quasi-static electromagnetic fields of cells in a living organism, comprising:
   a high-density array of passive sensor electrodes having a selectable spacing including at least one geometrically repeated pattern of sensor electrodes, whereby a uniform sensor electrode distribution overlays a region of interest on a surface of a living organism containing cells of clinical interest proximal to at least some of the sensor electrodes, and formed with a conductive electrolyte overlying each sensor electrode in the high-density array; and
   a quasi-static DC electrical potential measurement device configured to make measurements of an electrical potential at each sensor electrode of the high-density array on a measurement surface in the first region of interest;
   a processor configured to take a first measurement of an electrical potential of each electrode of the high-density array, take a second measurement of an electrical potential as a reference, determine a variability of the first measurement of the electrodes, set a normal control for mean values across the high-density array, and perform a convolution of each measurement at each location of the array, by averaging each array measurement with itself and its nearest neighbors wherein the processor performs the convolution at least three times.

2. The system of claim 1, having a density of at least about 25 electrodes per square inch.

3. The system of claim 2, having a density of at least about 100 electrodes per square inch.

4. The system of claim 1, wherein said electrode array has at least about 36 electrodes.

5. The system of claim 4, wherein said electrode array has at least about 100 electrodes.

6. The system of claim 5, wherein said electrode array has at least about 400 electrodes.

7. The system of claim 1, wherein said cells of clinical interest are selected from the group consisting of cells associated with DCIS, fibrocystic disease, cancer, tissue damage, inflammation, and changes associated with reproductive processes.

8. The system of claim 7, wherein said cancer is breast cancer.

9. The system of claim 7, wherein said cancer is testicular cancer.

10. The system of claim 7, wherein said cancer is liver cancer.

11. The system of claim 7, wherein said cancer is lung cancer.

12. The system of claim 7, wherein said cells are cancer cells responding to chemotherapy.

13. The system of claim 7, wherein said tissue damage is a continuing process which results from ongoing connective tissue disorders.

14. The system of claim 7, wherein said cells are associated with healing of tissue damage.

15. The system of claim 14, wherein said healing is soft tissue healing.

16. The system of claim 14, wherein said healing is bone healing.

17. The system of claim 7, wherein said inflammation comprises an inflammatory process responding to an infection.

18. The system of claim 7, wherein said reproductive process is selected from the group of processes consisting of fetal development and ovulation.

19. The system of claim 1, wherein said array is placed over a portion of an external surface of said living organism.

20. The system of claim 1, wherein said electrode array comprises a non-conductive material conformable to the surface having said electrodes spaced therein.

21. The system of claim 20, wherein said conformable material is contoured to the shape of said surface.

22. The system of claim 20, wherein said conformable material flexes over said surface.

23. The system of claim 1, wherein said electrodes are spaced regularly therein.

24. The system of claim 1, wherein said electrodes are spaced in a pattern designed to match the clinical application.

25. The system of claim 1, wherein said conductive material has an ionic content optimized for a stable signal connection to said surface.

26. The system of claim 25, wherein said ionic content is optimized to approximate the surface ionic content.

27. The system of claim 1, wherein said conductive material is a stabilized conductive medium.

28. The system of claim 1, wherein said conductive material contains water.

29. The system of claim 20, wherein said electrodes are formed in said non-conductive material by a printing process.

30. The system of claim 29, wherein said electrodes are formed by a metal/metal chloride polymer based ink.

31. The system of claim 30, wherein said ink contains silver/silver chloride.

32. The system of claim 1, wherein said electrodes are connected to electrically conductive trace lines.

33. The system of claim 32, wherein said trace lines are formed by a conductive polymer ink by the same printing process.

34. The system of claim 33, wherein said electrically conductive trace lines run along an extension of said non-conductive material, and away from said plurality of electrodes.

35. The system of claim 34 further comprising a housing secured to said extension and having electrical connections spaced to match the spacing of the trace lines along said extension of said non-conductive material.

36. The system of claim 1, further comprising connecting multiple A/D channels through a multiplexer to sequentially deliver the data collected from a multiple of electrodes.

37. The system of claim 1, further comprising an analog-to-digital converter coupled to each of said electrodes for generating a digital signal as a function of the electrical potential detected by said electrode means; and processing means coupled to said analog-to-digital converter for generating an output signal as a function of said digital signal.

38. The system of claim 1, wherein said electrodes are connected to a system capable of monitoring the electrode integrity.

39. The system of claim 1 wherein
   the processor further configured to reset a normal control across the high-density array by serially applying a weighted convolution to a normal control setting for each sensor electrode and the immediate neighbors of the sensor electrode resulting in a new dataset.

40. The system of claim 39 further comprising:

the repeated application of the unitary weighted convolution on the electrodes in the prior dataset including the sensor electrode and the immediate neighbors of the sensor electrode.

41. The system of claim 1 further comprising:

an index setting device configured to add the differences over the normal control settings for each sensor electrode after application of the weighted convolution collectively to obtain an first index rating.

42. The system of claim 39 further comprising:

an index setting device configured to add the differences over the reset normal control settings for each sensor electrode collectively after a second application of the weighted convolution to obtain a second index rating.

43. The system of claim 40 further comprising:

an index setting device configured to add the differences over the further reset normal control settings for each sensor electrode collectively after repeated application of the weighted convolution to obtain a third index rating.

44. The system of claim 41 further comprising:

assessing the clinical significance of the measurements made by the sensor electrodes of the high-density array based on the first index rating.

45. The system of claim 42 further comprising:

assessing the clinical significance of the measurements made by the sensor electrodes of the high-density array based on the second index rating.

46. The system of claim 43 further comprising:

assessing the clinical significance of the measurements made by the sensor electrodes of the high-density array based on the third index rating.

* * * * *